United States Patent [19]

Jéquier et al.

[11] Patent Number: 5,446,156
[45] Date of Patent: Aug. 29, 1995

[54] PROCESS FOR THE PREPARATION OF DIASTEREOISOMERIC PURE TETRAHYDROFOLATES

[75] Inventors: Pascal Jéquier, Melide; Fabrizio Marazza, Sorengo, both of Switzerland

[73] Assignee: Sapec S.A. fine chemicals, Switzerland

[21] Appl. No.: 994,308

[22] Filed: Dec. 21, 1992

[30] Foreign Application Priority Data

Dec. 21, 1991 [CH] Switzerland ............ 03799/91

[51] Int. Cl.⁶ ................ C07D 487/14; C07D 475/04
[52] U.S. Cl. ............................ 544/251; 544/258
[58] Field of Search ........................ 544/251, 258

[56] References Cited

U.S. PATENT DOCUMENTS

| | | | |
|---|---|---|---|
| 2,737,515 | 3/1956 | Brockman et al. | 544/251 |
| 4,959,472 | 9/1990 | Wood et al. | 544/258 |
| 5,006,655 | 4/1991 | Müller et al. | 544/258 |
| 5,134,235 | 7/1992 | Mueller et al. | 544/258 |
| 5,239,074 | 8/1993 | Marazza et al. | 544/251 |
| 5,300,505 | 4/1994 | Müller et al. | 544/251 |

OTHER PUBLICATIONS

PICHA et al, *Chemical Abstracts*, vol. 108, No. 112953 (1988) (Abstract of CS 237711).

*Primary Examiner*—Emily Bernhardt
*Attorney, Agent, or Firm*—Burns, Doane, Swecker & Mathis

[57] ABSTRACT

A process for the preparation of salts of (6R)-N(5),N(10)-methenyl-5,6,7,8-tetrahydrofolic acid of a particular formula (I). The process comprises:

(i) mixing at least one acid $S_1$ with an aqueous solution having dissolved therein an ammonium- or alkali metal-salt of (6RS)-N(10)-formyl-5,6,7,8-tetrahydrofolic acid of a particular formula (II) until a pH in the range of about 5.5 to 7.5 is obtained;

(ii) adding a water-soluble alkaline earth metal salt to the mixture obtained from step (i);

(iii) precipitating a solid and isolating the solid;

(iv) providing a solid of formula (I) by suspending the solid obtained from step (iii) in water, adding an acid $S_2$, which will not precipitate with an alkaline earth metal cation, until the pH stabilizes to a value of 1.0 to 2.0, and separating the resulting solid.

19 Claims, 3 Drawing Sheets

PROCESS FOR THE PREPARATION OF DIASTEREOISOMERIC PURE TETRAHYDROFOLATES

BACKGROUND OF THE INVENTION

The present invention is directed to a process for the preparation of diastereoisomeric pure tetrahydrofolates.

Processes for the preparation of reduced folates having a uniform (6S)- or (6R)-configuration are described in the International Patent Application PCT/FR 91/00185, as well as in the European Patent Application No. 91 105 715.6, publication No. 0 455 013 A1. Herein is described also the further prior art. With this reference these statements are deemed to be disclosed also herein.

SUMMARY OF THE INVENTION

It is a object of the present invention to provide a simple, cheap and industrial scale an realizable process, for the preparation of diastereoisomeric pure tetrahydrofolates, which process is also not detrimental to the environment.

The inventive process is directed to the preparation of salts of (6R)-N(5),N(10)-methenyl-5,6,7,8-tetrahydrofolic acid of the formula I

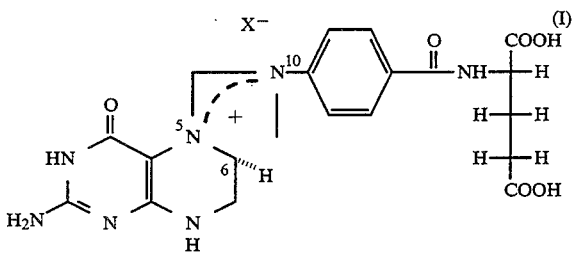

wherein X a formula (I) is an anion or an equivalent of an anion, and of the corresponding acid addition salts, and of the corresponding inner salts. According to the process of the invention, (i) at least one acid $S_1$ is mixed with an aqueous, or buffer containing aqueous, solution having dissolved therein an ammonium- or alkali metal-salt of (6RS) -N(10) -formyl-5,6,7,8-tetrahydrofolic acid of formula (II):

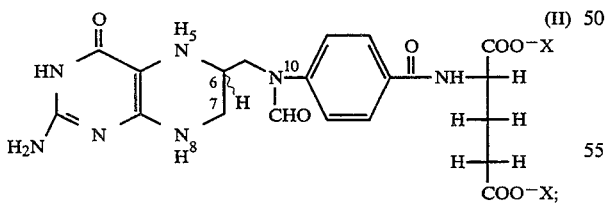

wherein X of formula (II) is an alkali metal cation or $NH_4^+$, preferably under an inert gas atmosphere, until a pH in the range of about 5.5 to 7.5 is obtained. Then, (ii) a water-soluble alkaline earth metal salt is added to the mixture obtained from step (i), and (iii) solid A is precipitated and isolated. A solid of formula (I) is then obtained by (iv) suspending solid A in water, adding an acid $S_2$, which will not precipitate with an alkaline earth metal cation, until the pH stabilizes to a value in the range of 1.0 to 2.0, preferably 1.5, and separating the resulting solid.

Figure 1:
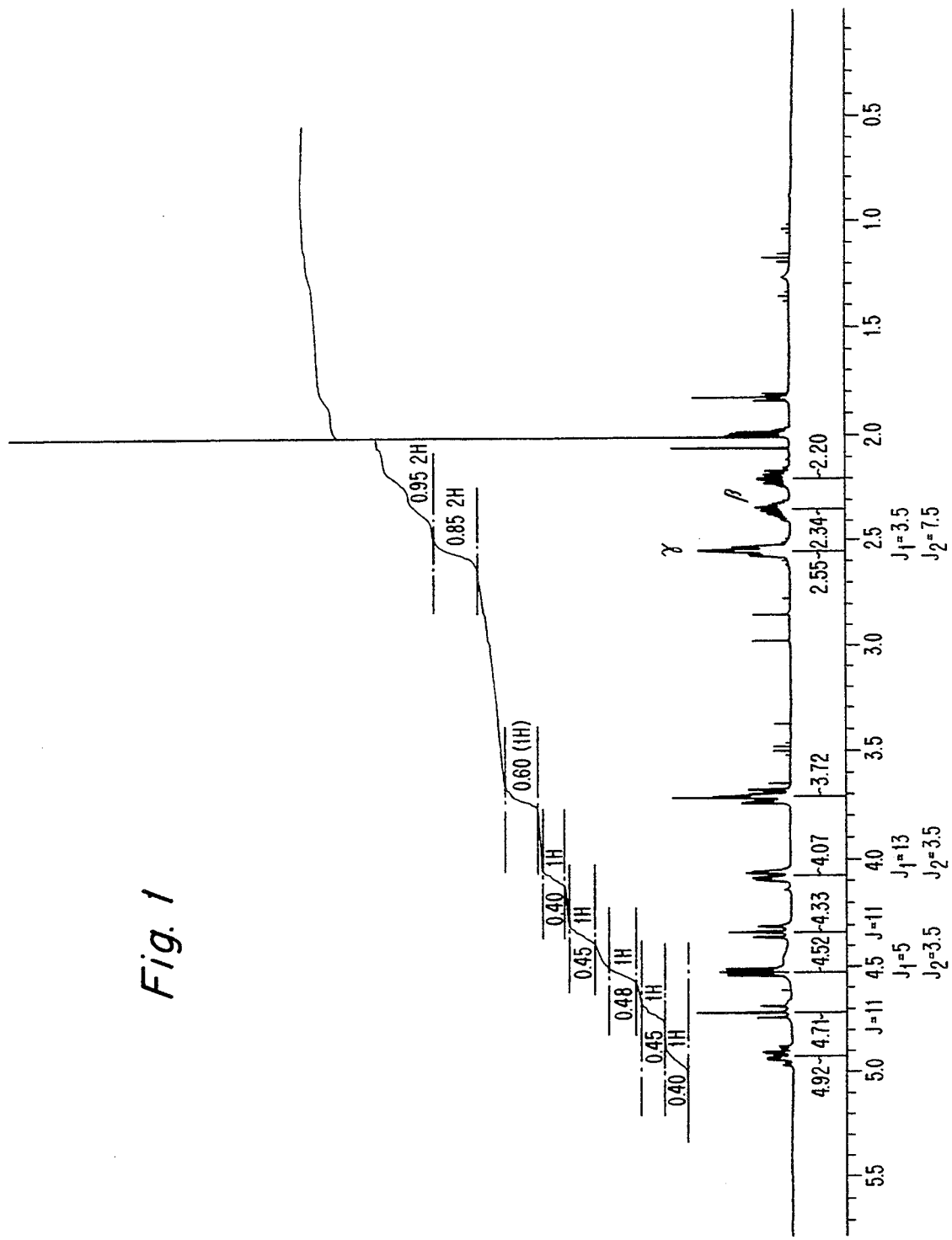
FIG. 1, FIG. 2 and FIG. 3 show parts of the $^1$H-NMR-spectra of the $Ca^{2+}$-salt of solid A, the $Mg^{2+}$-salt of solid A, and (6R)-methenyl-THF.Cl$^-$, respectively.

Preferred embodiments of this process are defined in the dependent claims.

DETAILED DESCRIPTION OF PREFERRED EMBODIMENTS

In the description below 5,6,7,8-tetrahydrofolic acid is sometimes abbreviated as THF.

As noted above, the process of the invention comprises (i) mixing at least one acid $S_1$ with an aqueous, or buffer containing aqueous, solution having dissolved therein an ammonium- or alkali metal-salt of (6RS)-N-(10)-formyl-5,6,7,8-tetrahydrofolic acid of formula (II):

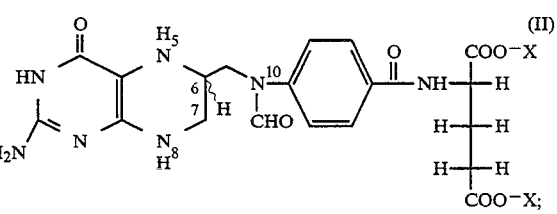

wherein X of formula (II) is an alkali metal cation or $NH_4^+$, until a pH in the range of about 5.5 to 7.5 is obtained. Then, (ii) a water-soluble alkaline earth metal salt is added to the mixture obtained from step (i), and (iii) solid A is precipitated and isolated. A solid of formula (I) is then obtained by (iv) suspending solid A in water, adding an acid $S_2$, which will not precipitate with an alkaline earth metal cation, until the pH stabilizes to a value in the range of 1.0 to 2.0, preferably 1.5, and separating the resulting solid.

Compounds of formula (II) can be obtained by adding a corresponding base to an aqueous, optionally a buffer containing, suspension, of a mixture of (6RS)-diastereoisomers of a salt of N(5),N(10)-methenyl-5,6,7,8-tetrahydrofolic acid of formula (III);

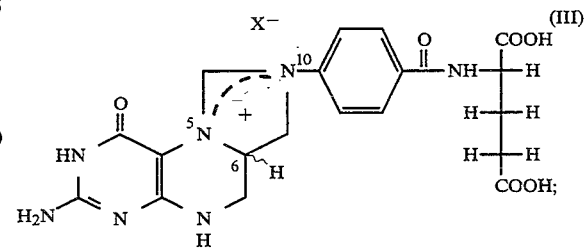

wherein X is an anion or equivalent of an anion, or of a corresponding acid addition salt, or of a corresponding inner salt. The aforementioned corresponding base is preferably sodium hydroxide or ammonia, and is added at a temperature in the range of from 20° C. to 60° C., most preferably 50° C., until a stable pH in the range of 7.5 to 9.0, preferably 8.3, is obtained.

Anion X of formula (I) is preferably a chloride or bromide.

Acid addition salts are preferably hydrochlorides, hydrobromides, organic sulfonates such as methane sulfonate, formates, oxalates, maleinates, trichloroacetates, or trifluoroacetates.

Acid $S_1$ is preferably selected from lower water-soluble carboxylic acids such as formic and acetic acid, and hydrohalic acids such as HCl and HBr. Preferably aqueous solutions of those acids are used.

It was according to the invention found that the acidification of an aqueous solution of an ammonium salt or of an alkaline earth metal salt of (6RS)-N(10)-formyl-THF, to a pH-value in a preferred range from 6.7 to 7.0 (e.g.) by means of a continuous addition of acid to a constant pH-value, followed by the subsequent addition of a water-soluble alkaline earth metal salt, affects the precipitation of solid A.

Acid $S_1$ and the alkaline earth metal salt are preferably added under temperature conditions of from 0° C. to 60° C., more preferably 10° C. to 40° C.

The alkaline earth metal salt is preferably a corresponding salt of a lower, water soluble carboxylic acid, especially a formate, an acetate, or a halide, preferably a chloride or bromide. Corresponding magnesium and calcium salts are preferred.

The alkaline earth metal salt is preferably used in an amount of from 0.5 to 1.0, more preferably 0.7, mole equivalents, based on the amount of compound of formula II.

For the process of the invention, the starting material, (6RS)-N(10)-formyl-THF, can be prepared for example from (6RS)-methenyl-THF.Cl$^-$ according to the Swiss Patent Application No. 02 933/91-9 and the references disclosed herein.

When the above mentioned solid A is dissolved in a suitable solvent, for example in water or formamide, and is analyzed by means of HPLC, then the obtained peak shows a retention time, which is identical with that, which is obtained with methenyl-THF. For that reason it can be assumed, that the solid A shows the partial structure of methenyl-THF.

In addition, the mass spectras (FAB/Matrix=thioglycerin) show the same m+=456.

The elemental analysis of the solid A shows the presence of a half equivalent of an alkaline earth metal cation (Ca$^{2+}$ or Mg$^{2+}$) and is in agreement with the following summation formula:

$C_{20}H_{20}N_7O_6Me_{0.5}$ wherein Me is an alkaline earth metal cation (e.g. Ca$^{2+}$ or Mg$^{2+}$).

In the following part it is pointed to the differences of the $^1$H-NMR-spectras (400 MHz/detected in d$_3$-formamide) of (6R)-methenyl-THF.Cl$^-$ and of the solid A (Ca$^{2+}$ and Mg$^{2+}$ salt).

FIG. 1 shows a part of the $^1$H-NMR-spectra of the Ca$^{2+}$-salt of the solid A.

Figure 2:
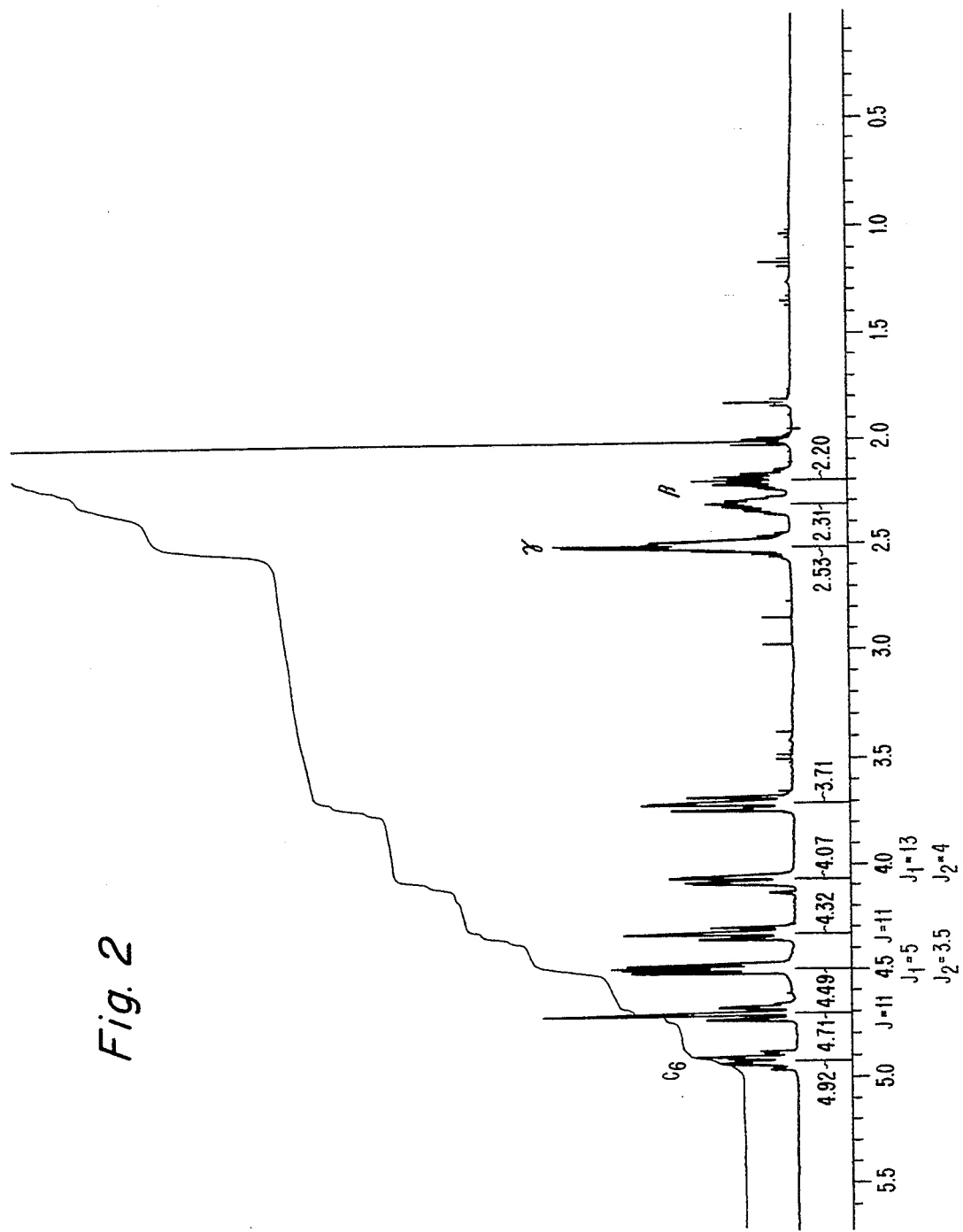

FIG. 2 shows a part of the $^1$H-NMR-spectra of the Mg$^{2+}$-salt of the solid A.

Figure 3:
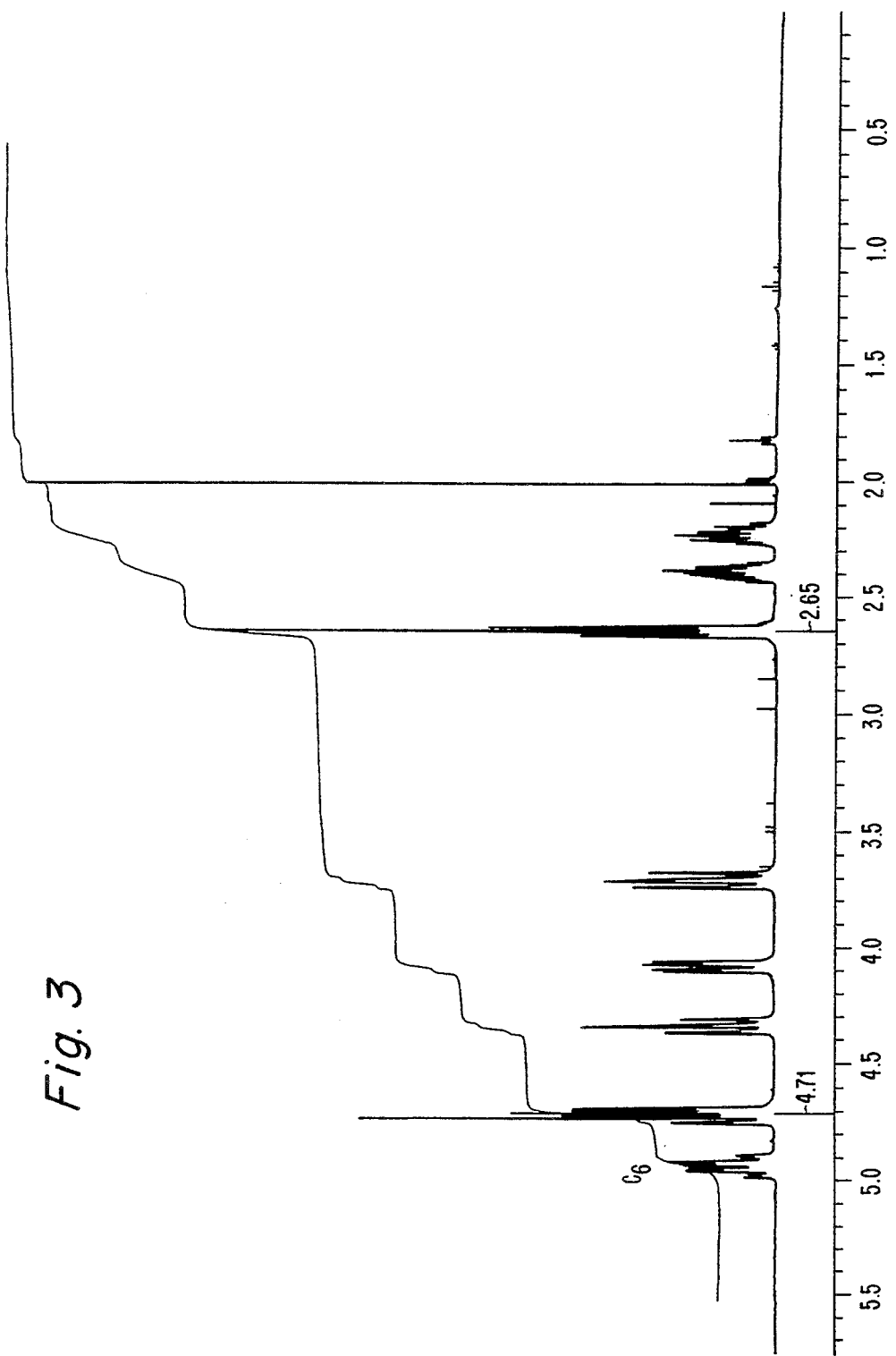

FIG. 3 shows a part of the $^1$H-NMR-spectra of (6R)-methenyl-THF.Cl$^-$.

In the spectras of the Ca$^{2+}$- and Mg$^{2+}$-salts all 15 hydrogen atoms bound to C-atoms give sharp and separated signals.

In the spectra of (6R)-methenyl-THF.Cl$^-$ a multiplet is observed at 4.71 ppM, which corresponds integrated to 2 protons.

Contrary to this, in the Ca$^{2+}$- and Mg$^{2+}$-salts, two separate signals are observed:
4.52 (1H) and 4.71 (1H) for the Ca2+-salt and 4.49 (1H) and 4.71 (1H) for the Mg$^{2+}$-salt, respectively.

In addition in the case of (6R)-methenyl-THF.Cl$^-$ the $\gamma$-CH$_2$ group of the glutamate side chain gives a sharp triplet at 2.65 ppM. Contrary to this in the case of the Ca$^{2+}$- and Mg$^{2+}$-salts for this group a multiplet is observed at 2.55 ppM, and 2.53 ppM, respectively.

The above data allow for the conclusion, that the solid A shows the structure of the formula IV.

Thus, there are found quite surprisingly hemialkaline earth metal salts of N(5),N(10)-methenyl-THF.

These alkaline earth metal salts show quite surprisingly show a selective crystallization behaviour which may be used for the accumulation of the (6R)-form.

When such a salt is reduced to N(5)-methyl-THF and is then analyzed on a chiral column, a diastereoisomeric purity of the (6S)-form from 85 to 95% is is noted.

The acid $S_2$ must be a strong acid, and should not allow a precipitation with an alkaline earth metal cation. As acid $S_2$ sulfuric acid and phosphoric acid are unsuitable. Hydrochloric acid is preferred, especially aqueous hydrochloric acid. Other suitable acids include p-toluene-sulfonic acid, trifluoroacetic acid and trichloroacetic acid.

When the resulting alkaline earth metal salts are treated with aqueous hydrochloric acid (pH about 1), then the known compound (6R)-N(5),N(10)-methenyl-THF.Cl$^-$ of the formula I is obtained; see the Swiss Patent Application No. 02 794/91-0.

According to known processes the compound of formula I may be transformed either by means of a reduction into (6S)-N(5)-methyl-THF.Ca$^{2+}$ (see: White, Bailey and Goldman, J. Biol. Chem., (1978), 253,242) or by means of a hydrolysis into (6S)-N(5)-formyl-THF.Ca$^{2+}$ (see: CH PS 305 574).

It has also be found, that the resulting alkaline earth metal salts may be transformed directly into (6S)-alkaline earth metal folinates, especially into (6S)-calciumfolinate. There can be provided by the invention hemi-alkaline earth metal salts of N(5), N(10)-methenyl-5,6,7,8 -tetrahydrofolic acid of the following formula (IV'):

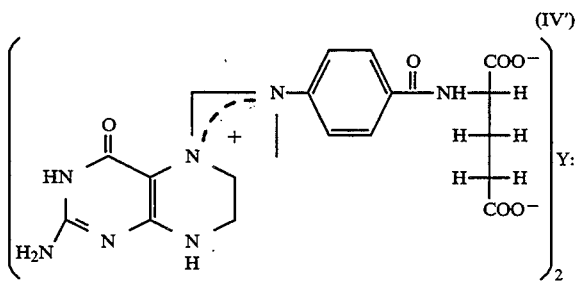

wherein Y is an alkaline earth metal cation, preferably Ca$^{2+}$ or Mg$^{2+}$; in the form of a (6RS)-diastereoisomer mixture, or in the form of single (6R)- or (6S)-diastereoisomers.

In a preferred embodiment of the invention, there is provided a process for the preparation of hemi-alkaline earth metal salts of (6R)-N(5),N(10)-methenyl-5,6,7,8-tetrahydrofolic acid of formula (IV):

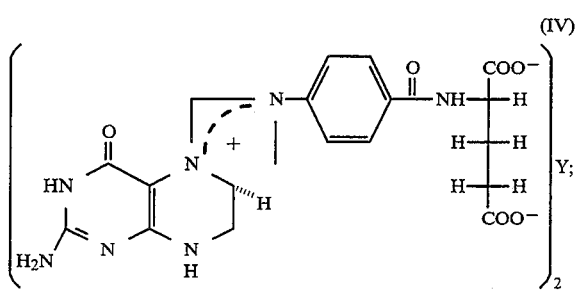

wherein Y is an alkaline earth metal cation, especially $Ca^{2+}$ or $Mg^{2+}$. According to the process, at least one acid $S_1$ is mixed with an aqueous or buffer containing aqueous, solution having dissolved therein an ammonium or alkali metal salt of (6RS)-N(10)-formyl-5,6,7,8-tetrahydrofolic acid of formula (II), preferably under an inert gas atmosphere, until a pH of from 5.5 to 7.5 is obtained. Then a water-soluble alkaline earth metal salt is added to the mixture and a solid A of formula (IV) is obtained and isolated.

Also provided by the invention is a process for the preparation of alkaline earth metal salts of (6S)-N(5)-formyl-5,6,7,8-tetrahydrofolic acid of formula (V);

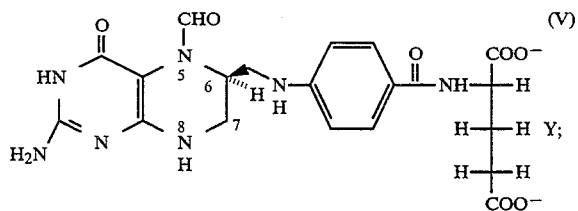

wherein Y is an alkaline earth metal cation, preferably $Ca^{2+}$ or $Mg^{2+}$. According to the process, at least one acid $S_1$ is mixed with an aqueous, or buffer containing aqueous, solution having dissolved therein an ammonium or alkali metal salt of (6RS)-N(10)-formyl-5,6,7,8-tetrahydrofolic acid of formula (II), preferably under an inert gas atmosphere, until a pH of from 5.5 to 7.5 is obtained. Thereafter, a water-soluble alkaline earth metal salt is added, and a solid A is obtained and isolated. The solid A is then suspended in water and heated under an inert gas atmosphere to a temperature of from 70° C. to 100° C. while maintaining the pH at 5.0 to 8.0 by continuously adding an aqueous solution or suspension of a base, such as an alkaline earth metal hydroxides, -carbonates and -hydrogen carbonates. The obtained solution can then be cooled to a temperature of from 30° C. to 50° C., and the pH increased to a level of 6.5 to 8.5, by adding one of the aforementioned bases. The solution can then be concentrated to e.g., about ¾ of the original volume at a temperature of at least 45° C., followed by cooling the concentrated solution slowly e.g., over about 24 hours, to room temperature to obtain a solid of formula (V). The solid of formula (V) can then be separated. Preferably the base is calcium or magnesium hydroxide.

The following examples shall illustrate the present invention.

EXAMPLE 1

To a suspension of 50 g of (6RS)-methenyl-THF.Cl⁻ in 450 ml of water, stirred under a nitrogen atmosphere at a temperature of 50° C., were added dropwise 20% NaOH until a stable measured pH-value of 8.3 was reached.

A HPLC-analysis of the obtained mixture showed no methenyl-THF, but the presence of a new peak, which has been attributed to the formed N(10)-formyl-THF.Na$_2$.

To the obtained solution were then added at a temperature of 40° C., 30% aqueous acetic acid, until the mixture showed a pH-value of 6.8. Then were added 12 g of calcium acetate, and the mixture was stirred further at the same temperature, whereby a product began to crystallize. Then during 3 hours 8 ml of 30% aqueous acetic acid were added drop by drop. The mixture showed then a pH-value of 6.8.

The so obtained crystallization product was filtered off, washed twice with water and twice with acetone and it was finally dried at a temperature of 60° C. under reduced pressure, whereby 12 g of a yellow solid were isolated (25% w/w yield).

The HPLC analysis on a reversed phase (RP)-column showed a 95% chemical purity.

IR (KBr): 3392, 3220, 3095, 2930, 1650, 1601, 1559, 1510, 1450, 1400, 1341, 1318, 1289, 1243, 757 cm$^{-1}$. MS (FAB/Matrix: Thioglycerin): m$^+$=456 UV (20 mg/l in $H_2O$/HCONH$_2$99:1): $\lambda_{max}$=360.5 nm $\lambda_{min}$=303.5 nm $A_{max}/A_{min}$=4.24

| | elemental analysis | | | |
|---|---|---|---|---|
| | % C | % H | % N | % Ca |
| Theory for $C_{20}H_{20}N_7O_6Ca_{0.5} \times 4\ H_2O$ | 43.97 | 5.17 | 17.95 | 3.67 |
| experimental values | 43.94 | 4.85 | 17.65 | 3.21 |

For the determination of the diastereoisomeric purity 15 mg of the above mentioned crystals were dissolved 1.5 ml of a 1.8% solution of p-toluene sulfonic acid. Then were added 6 mg NaBH$_3$CN, and the mixture was stirred for 30 minutes at room temperature. Thereby the crystals were transformed completely into N(5)-methyl-THF. The analysis of the latter compound by means of a chiral HPLC-column (RESOLVOSIL) showed a diastereoisomeric purity of 90% (6S).

$^1$H-NMR Spektra (400 MHz/in d$_3$-Formamid/Ref.: TMS): 9.66 (1H,s); 8.06 (2H,d); 7.48 (2H,d); 4.92 (1H,dq); 4.71 (1H,t); 4.51 (1H,dd); 4.33 (1H,t); 4.07 (1H,dd); 3.71 (1H,m); 2.55 (2H,dt); 2.34 (1H,m); 2.20 (1H,m).

EXAMPLE 2

Starting with 50 g of (6RS)-methenyl-THF.Cl⁻, in analogy to the way as described in example 1, a solution of N(10)-formyl-THF.Na$_2$ was prepared. At room temperature 30% aqueous acetic acid was added dropwise until a pH-value of 6.9 was obtained. Then 15 g of solid magnesium acetate tetrahydrate were added, and the mixture was stirred at the same temperature, whereby a crystalline solid began to separate. Simultaneously the pH-value was kept between 6.8 and 7.0 by means of a dropwise addition of 8 ml of 30% aqueous acetic acid for 10 hours.

The obtained solution was then cooled to a temperature of 0° C., and stirred for 1 hour at that temperature. The crystallisate was isolated by means of filtration, washed 3 times with H$_2$O and twice with acetone, and dried during 2 hours under reduced pressure at a temperature of 60° C.

Yield: 14 g (28% w/w) of a yellow solid.

The HPLC analysis on a RP-solumn showed a 95% chemical purity.

IR (KBr): 3340, 3110, 2950, 1630, 1600, 1560, 508, 1450, 1405, 1318, 1289, 1243, 763, 657, 612 cm$^{-1}$. MS (FAB/Matrix: Thioglycerin): m$^+$=456 UV (20 mg/l in $H_2O$/HCONH$_2$99:1): $\lambda_{max}$=359 nm $\lambda_{min}$=301 nm $A_{max}/A_{min}$=4.24 Komplexometric Titration of Magnesium: 2.35% Mg (theoretical value, amended for the $H_2O$ content: 2.31%).

For the determination of the diastereoisomeric purity, 15 mg of the above mentioned crystals were dissolved in 1.5 ml of a 1.8% solution of p-toluene sulfonic acid. Then were added 6 mg NaBH3CN, and the mixture was stirred during for 30 minutes at room temperature. Thereby the crystals were transformed completely into N(5)-methyl-THF. The analysis of the latter compound by means of a chiral HPLC-column (RESOLVOSIL) showed a diastereoisomeric purity of 88% (6S).

$^1$H-NMR Spektra (400 MHz/in d3-Formamid/Ref.: TMS): 9.66 (1H,s); 8.06 (2H,d); 7.47 (2H,d); 4.92 (1H,dq); 4.71 (1H,t); 4.49 (1H,dd); 4.32 (1H,t); 4.07 (1H,dd); 3.71 (1H,m); 2.53 (2H,m); 2.31 (1H,M); 2.20 (1H,m).

EXAMPLE 3

20 g of the product, prepared according to example 1, were suspended in 200 ml of water at a temperature of 30° C. Then was added dropwise 18% aqueous hydrochloric acid, until the measured pH-value of the resulting mixture has stabilized to a value of 1.3.

This mixture was stirred at a temperature of 30° C. for 30 minutes.

The solid was filtered off, washed twice with water and twice with acetone, and finally dried at a temperature of 60° C. under reduced pressure.

There were obtained 18.4 g of a yellow solid, namely (6R)-N(5),N(10)-methenyl-THF-chloride.

The HPLC analysis on a RP-column showed a 100% chemical purity (detection at 354 nm).

There was obtained the same diastereoisomeric purity as described in example 1.

EXAMPLE 4

Transformation of the (6R)-hemi calcium salt into (6S)-calcium folinate 100.0 g of the hemi calcium salt of (6R)-N(5),N(10)-methenyl-THF, obtained as described in example 1, were warmed in 800 ml of water under a nitrogen atmosphere at a temperature of 80° C.

The pH-value of the mixture was kept at 5.8 during the reaction by means of a continuous addition of a 25% aqueous suspension of calcium hydroxide.

After 12 hours heating at 80° C., the obtained (6S)-N(5)-formyl-THF solution was cooled to a temperature of 30° C., treated with 5.0 g of charcoal, and adjusted to a pH-value of 7.5, by means of the addition of an aqueous calcium hydroxide suspension.

The obtained mixture was then filtered through a layer of celite and concentrated to a volume of 600 ml under reduced pressure and at a temperature of 50° C.

The obtained solution was then cooled for 32 hours slowly and controlled from 50° C. to room temperature, whereby the desired (6S)-calcium-folinate crystallized.

The product was filtered off and crystallized once more from water.

By means of filtration, the obtained crystallisate was washed once with water and once with 94% ethanol, and dried under reduced pressure at a temperature of 50° C.

In this way 42.0 g of the pure (6S)-calcium-folinate were isolated.

The HPLC-analysis on a RP-column showed a chemical purity of 99.6%.

The comparison with the reference substance [USP standard/(6RS)-mixture], also by means of HPLC, gave a content of 97.3%.

The diastereoisomeric purity was tested on a chiral HPLC-column (RESOLVOSIL), whereby a value of 99.3% was obtained.

Determination of the water content according to Karl Fischer: 14%.

Gaschromatographical determination of ethanol: 0.6%.

Komplexometric determination of Calcium: 8.0% (theorie: 7.84%).

We claim:

1. A method for the preparation of salts of (6R)-N(5),N(10)-methenyl-5,6,7,8-tetrahydrofolic acid of the following formula (I):

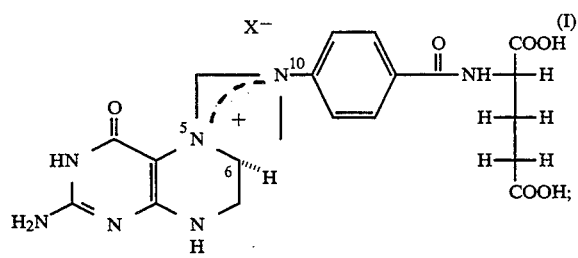

wherein X is an anion selected from chloride or bromide, or of an acid addition salt of (6R)-N(5),N(10)-methenyl-5,6,7,8 -tetrahydrofolic acid selected from a hydrochloride, hydrobromide, methane sulfonate, formate, oxalate, maleate, trichloroacetate, trifluoroacetate thereof, or of a corresponding inner salt of (6R)-N(5),N(10)-methenyl-5,6,7,8 tetrahydrofolic acid, said method comprising:

(i) mixing at least one acid $S_1$, wherein $S_1$ is a lower water-soluble carboxylic acid or a hydrohalic acid, with an aqueous solution having dissolved therein an ammonium- or alkali metal-salt of (6RS)-N(10)-formyl-5,6,7,8-tetrahydrofolic acid of formula (II):

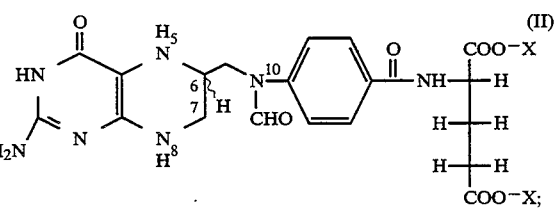

wherein X of formula (II) is an alkali metal cation or $NH_4^+$, until a pH in the range of about 5.5 to 7.5 is obtained;

(ii) adding a water-soluble alkaline earth metal salt to the mixture obtained from step (i);

(iii) precipitating a hemi-alkaline earth metal salt of N(5),N(10)-methenyl-5,6,7,8-tetrahydrofolic acid as a solid A and isolating said solid;

(iv) providing a solid of formula (I) by suspending solid A obtained from step (iii) in water, adding an acid S₂, wherein S₂ is selected from the group consisting of hydrochloric acid, p-toluene-sulfonic acid, methane sulfonic acid, trifluoroacetic acid, and trichloroacetic acid, which will not precipitate with an alkaline earth metal cation, until the pH stabilizes to a value of 1.0 to 2.0, and separating the resulting solid.

2. A method according to claim 1, wherein an acid S₂ is added in step (iv) until the pH stabilizes to a value of about 1.5.

3. A method according to claim 1, wherein compounds of formula (II) are obtained by adding a corresponding base to an aqueous suspension of a mixture of (6RS)-diastereoisomers of a salt of N(5),N(10)-methenyl-5,6,7,8-tetrahydrofolic acid of formula (III);

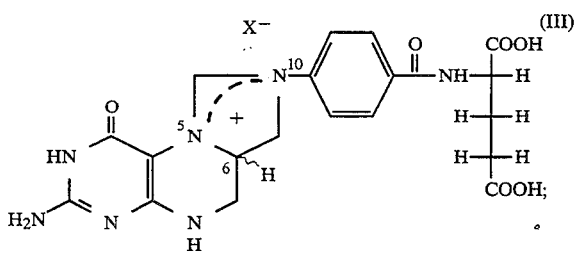

wherein X is an anion selected from chloride or bromide, or of an acid addition salt of (6R)-N(5),N (10)-methenyl-5,6,7,8-tetrahydrofolic acid selected from a hydrochloride, hydrobromide, methane sulfonate, formate, oxalate, maleate, trichloroacetate, or trifluoroacetate thereof, or of a corresponding inner salt of (6R)-N(5),N(10)-methenyl-5,6,7,8 tetrahydrofolic acid.

4. A method according to claim 3, wherein the aqueous suspension contains a buffer.

5. A method according to claim 3, wherein the corresponding base is sodium hydroxide or ammonia, and is added at a temperature in the range of from 20° C. to 60° C., until a stable pH in the range of 7.5 to 9.0, is obtained.

6. A method according to claim 1, wherein the acid addition salt is methane sulfonate.

7. A method according to claim 1, wherein acid S₁ is formic acid, acetic acid, HCl and/or HBr.

8. A method according to claim 1, wherein acid S₁ is added in the form of an aqueous solution.

9. A method according to claim 1, wherein acid S₁ and the alkaline earth metal salt are added under temperature conditions of from 0° C. to 60° C.

10. A method according to claim 9, wherein acid S₁ and the alkaline earth metal salt are added under temperature conditions of from 10° C. to 40° C.

11. A method according to claim 1, wherein the alkaline earth metal salt is a corresponding salt of a lower, water soluble carboxylic acid, an acetate, or a halide.

12. A method according to claim 11, wherein the alkaline earth metal salt is a corresponding salt of a formate, an acetate, a chloride or bromide.

13. A method according to claim 11, wherein the alkaline earth metal salt is a magnesium or calcium salt.

14. A method according to claim 1, wherein the alkaline earth metal salt is added in an amount of from 0.5 to 1.0 equivalents, based on the amount of compound of formula (II).

15. A method according to claim 14, wherein the alkaline earth metal salt is added in an amount of about 0.7 equivalents, based on the amount of compound of formula (II).

16. A process for the preparation of hemialkaline earth metal salts of (6R)-N(5),N(10)-methenyl-5,6,7,8-tetrahydrofolic acid of formula (IV):

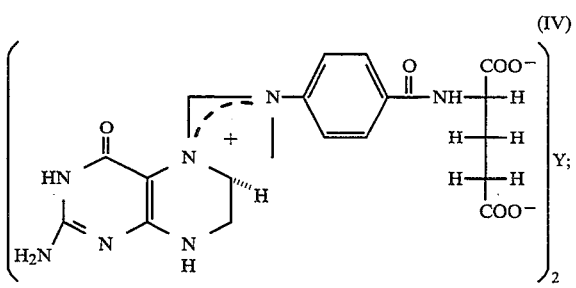

wherein Y is an alkaline earth metal cation, said process comprising mixing at least one acid S₁, wherein S₁ is a lower water-soluble carboxylic acid or a hydrohalic acid, with an aqueous solution having dissolved therein an ammonium or alkali metal salt of (6RS)-N(10)-formyl-5,6,7,8-tetrahydrofolic acid of formula (II):

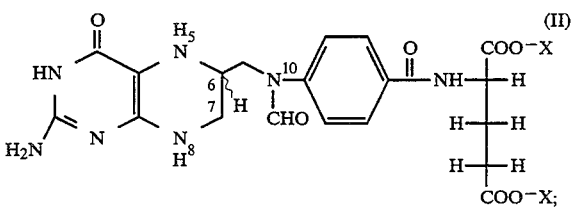

wherein X is an alkali metal cation or NH₄⁺, until a pH of from 5.5 to 7.5 is obtained, adding a water-soluble alkaline earth metal salt to the mixture, and obtaining and isolating a solid of formula (IV).

17. A process according to claim 16, wherein Y is Ca²⁺ or Mg²⁺.

18. A process according to claim 16, wherein said at least one acid S₁ is mixed with the ammonium or alkali metal salt of (6RS)-N(10)-formyl-5,6,7,8-tetrahydrofolic acid of formula (II) under an inert gas atmosphere.

19. A process according to claim 16, wherein the aqueous solution having dissolved therein an ammonium or alkali metal salt of (6RS)-N(10)-formyl-5,6,7,8-tetrahydrofolic acid of formula (II) comprises a buffer.

* * * * *